(12) United States Patent
Bateman et al.

(10) Patent No.: US 7,432,501 B2
(45) Date of Patent: Oct. 7, 2008

(54) IONISING PARTICLE ANALYSER ENABLING FOR EXAMPLE THE SEPARATION OF THE FLUORESCENT YIELD (FY) AND THE TOTAL ELECTRON YIELD (TEY) IN EXAPS (EXTENDED X-RAY ABSORPTION FINE STRUCTURE) MEASUREMENTS

(75) Inventors: James Edmond Bateman, Oxon (GB); Gareth Derbyshire, Oxon (GB)

(73) Assignee: Council for the Central Laboratory of the Research Councils, Cheshire (GB)

( * ) Notice: Subject to any disclaimer, the term of this patent is extended or adjusted under 35 U.S.C. 154(b) by 406 days.

(21) Appl. No.: 10/571,183

(22) PCT Filed: Aug. 27, 2004

(86) PCT No.: PCT/GB2004/003680

§ 371 (c)(1),
(2), (4) Date: Mar. 9, 2006

(87) PCT Pub. No.: WO2005/024405

PCT Pub. Date: Mar. 17, 2005

(65) Prior Publication Data

US 2007/0051898 A1 Mar. 8, 2007

(30) Foreign Application Priority Data

Sep. 9, 2003 (GB) ............................. 0321039.0

(51) Int. Cl.
*G01N 23/223* (2006.01)

(52) U.S. Cl. .................. 250/294; 250/304; 378/44; 378/45; 378/46; 378/47; 378/49; 378/50

(58) Field of Classification Search .................. None
See application file for complete search history.

(56) References Cited

U.S. PATENT DOCUMENTS 4,484,339 A * 11/1984 Mallozzi et al. ............... 378/82

(Continued)

FOREIGN PATENT DOCUMENTS

EP            1 012 587           1/2003

(Continued)

OTHER PUBLICATIONS

R. A. Rosenberg, J. K. Simons, and S. P. Frigo, "X-ray fluorescence detection of low-Z elements using a microchannel plate detector," *Review of Scientific Instruments*, vol. 63, No. 4, Part 1, Apr. 1992, p. 2193-2194, XP002305295, 1992, American Institute of Physics.

(Continued)

*Primary Examiner*—David A. Vanore
(74) *Attorney, Agent, or Firm*—Michael Best & Friedrich LLP

(57) ABSTRACT

An ionising particle analyser comprises a source of ionising particles, a charged particle detector, and an ionisable gas located between the source and the detector. The analyser further comprises a charged particle impeding device located between the source and the detector. The charged particle impeding device is arranged to be maintained in a first configuration at a potential to impede the passage of charged particles and pass uncharged particles.

17 Claims, 3 Drawing Sheets

U.S. PATENT DOCUMENTS

| | | | | |
|---|---|---|---|---|
| 4,558,223 | A | * | 12/1985 | Broadhurst et al. .......... 250/374 |
| 4,652,866 | A | * | 3/1987 | Siegmann et al. ........... 340/628 |
| 4,752,685 | A | * | 6/1988 | Shiokawa et al. ........... 250/305 |
| 4,959,848 | A | * | 9/1990 | Parobek ...................... 378/46 |
| 5,038,043 | A | | 8/1991 | Dorion et al. |
| 5,166,519 | A | * | 11/1992 | Turner ........................ 250/305 |
| 5,249,216 | A | * | 9/1993 | Ohsugi et al. ................. 378/46 |
| 5,365,563 | A | * | 11/1994 | Kira et al. ..................... 378/48 |
| 6,173,037 | B1 | * | 1/2001 | Brouwer ..................... 378/45 |
| 6,233,307 | B1 | * | 5/2001 | Golenhofen ................. 378/45 |
| 6,314,158 | B1 | * | 11/2001 | Shiota et al. .................. 378/48 |
| 6,448,097 | B1 | * | 9/2002 | Singh et al. ................... 438/16 |
| 6,452,401 | B1 | * | 9/2002 | Derbyshire et al. ......... 324/464 |
| 6,577,704 | B1 | * | 6/2003 | Holz ........................... 378/44 |
| 6,804,595 | B1 | * | 10/2004 | Quail et al. ................... 701/45 |
| 6,917,153 | B2 | * | 7/2005 | Oskam et al. ............... 313/483 |
| 6,934,659 | B2 | | 8/2005 | Polzin ........................ 702/140 |
| 6,937,691 | B2 | * | 8/2005 | Yamagami et al. ............ 378/45 |
| 7,206,375 | B2 | * | 4/2007 | Chen et al. .................... 378/51 |
| 7,233,643 | B2 | * | 6/2007 | Sipila et al. ................... 378/44 |
| 7,287,322 | B2 | * | 10/2007 | Mathieu et al. ............... 29/842 |

FOREIGN PATENT DOCUMENTS

| | | |
|---|---|---|
| GB | 1 209 788 | 10/1970 |
| JP | 2001166059 | 6/2001 |
| WO | WO 9306470 | 4/1993 |
| WO | WO 98/36268 | 8/1998 |
| WO | WO 99/64891 | 12/1999 |

OTHER PUBLICATIONS

Masoud Kasrai et al, "X-ray fluorescence measurements of X-ray absorption near edge structure at the Si, P, and S L edges," *Journal of Vacuum Science & Technology A (Vacuum, Surfaces, and Films)*, vol. 11, No. 5, Sep.-Oct. 1993, p. 2694-2699, XP002305296, ISSN: 0734-2101, p. 2694, right-hand column, p. 2695, right-hand column, paragraph 2, American Vacuum Society, USA.

J. E. Bateman et al, "Studies of the Gain Properties of Microstrip Gas Counters Relevant to Their Application as X-Ray and Electron Detectors," *IEEE Transactions on Nuclear Science*, vol. 49, No. 4, Aug. 2002, p. 1644-1650, XP002305297, p. 1649, 2002, IEEE Nuclear and Plasma Sciences Society.

G. Tourillon et al, "Electron yield X-ray absorption spectroscopy at atmospheric pressure," *Physics Letters A*, vol. 121, No. 5, Apr. 27, 1987, p. 251-257, XP009039581, ISSN: 0375-9601, p. 251 and p. 255, Elsevier Science Publishers B.V., The Netherlands.

M. E. Kordesch and R. W. Hoffman, "Electron-yield extended X-ray absorption fine structure with the use of a gas-flow electron detector," *Physical Review B (Condensed Matter) USA*, vol. 29, No. 1, Jan.-Jun. 1984, p. 491-492, XP002305299, ISSN: 0163-1829, entire document, The American Physical Society.

* cited by examiner

IONISING PARTICLE ANALYSER ENABLING FOR EXAMPLE THE SEPARATION OF THE FLUORESCENT YIELD (FY) AND THE TOTAL ELECTRON YIELD (TEY) IN EXAPS (EXTENDED X-RAY ABSORPTION FINE STRUCTURE) MEASUREMENTS

The present invention relates to an apparatus and method for analysing ionising particles using an ionisable gas.

Measurement of electron yield is a known technique which is used to study the response of material surfaces to interactions with beams of high energy photons such as X-rays. Exposing the surface of a material to X-rays of varying energies, and measuring the number and energy of electrons emitted from the surface, makes it possible to analyse the chemical characteristics of the surface in detail.

The total electron yield (TEY) of the emissive electrons includes both electrons emitted by the photoelectric effect and by the Auger effect. The energies of the Auger electrons emitted are characteristic of the atomic energy levels, providing a method of determining surface composition and character. However, instead of emitting an Auger electron, energy may be lost from the material as a X-ray. The fluorescent yield (FY) is the probability of a specific excited atom emitting a photon in preference to an Auger electron.

In the study of the surface layers of material, emission EXAFS (Extended X-ray Absorption Fine Structure) is a well-established technique, exploited extensively in conjunction with synchrotron X-ray light sources around the world. The technique utilises X-rays to excite the atoms that are close to the surface of the material, resulting in X-ray and electron emissions which can be measured to provide information on the atomic structure of the sample material.

European patent application 98903130.7 describes an extension of the basic surface EXAFS technique. The charged particle detector comprises at least one pair of electrodes (i.e. an anode and a cathode). The application describes a charged particle analyser comprising a charged particle detector spaced apart from a sample material which is the source of charged particles, with both the sample and the detector immersed in an ionisable gas. Primary particles are those particles emitted from the source (i.e. the sample material). By maintaining the detector at a positive potential relative to the sample, secondary electrons generated by the fast primary electrons emitted from the sample will be drifted towards the detector. X-rays emitted from the material may also act to ionise the gas to produce secondary electrons. The resulting cloud of secondary ionised gas electrons drifts in the electric field towards the detector, with the amplified signal being collected at the anodes of the detector. This amplified signal can contain information on both the X-rays and the electrons emitted from the sample.

By analysing the distribution (i.e. spectrum) of pulse heights from the detector, an analysis of the surface layer to a controlled depth can be performed.

It is an aim of the embodiments of the present invention to provide a particle analyser that substantially addresses one or more of the problems of the prior art, whether referred to herein or otherwise. It is particularly an aim of embodiments of the present invention to provide a particle analyser that provides improved information about the structure of a sample, preferably at various depths below the surface.

According to a first aspect, the present invention provides an ionising particle analyser comprising a source of ionising primary particles, a charged particle detector, an ionisable gas located between the source and the detector and wherein the analyser further comprises a charged particle impeding device located between the source and the detector, and arranged to be maintained in a first configuration at a potential to impede the passage of secondary electrons generated by charged primary particles ionising the gas and pass uncharged primary particles.

By providing a particle analyser having such a structure, uncharged (i.e. electrically neutral) ionising particles from the source can pass the charged particle impeding device. Such uncharged particles (e.g. photons) may then ionise the gas, with the subsequent secondary electrons being detected by the charged particle detector. Thus, the signal arising from the uncharged particles may be measured independently of the charged particles, providing further information on the structure of the sample.

The charged particles emitted by the sample may comprise electrons and the uncharged particles may comprise photons.

The charged particle impeding device may be held at a potential to repel the secondary electrons generated in the gas by the charged primary particles.

The charged particle impeding device may comprise at least one bar lying in a plane substantially parallel to a surface of the sample.

The charged particle impeding device may comprise a grid comprising a plurality of substantially parallel bars.

The charged particle impeding device may be further arranged to be maintained in a second configuration that allows the substantially unimpeded passage of both charged particles and uncharged particles.

The charged particle impeding device may be located within the ionisable gas, and spaced from the source such that charged particles emitted from the source will have been substantially completely converted to ionised gas electrons prior to being incident upon the charged particle impeding device.

The source may be a sample and means may be provided for exposing the sample to a beam of radiation, the energy of which is sufficient to cause ionising particles to be emitted from the sample.

The exposing means may comprise an X-ray source.

The sample may define a surface which is substantially planar and the beam may be directed towards the sample in a direction inclined to a normal to the sample surface.

The beam may be directed at a glancing angle relative to the sample surface.

The beam may be arranged to pass between the source and the charged particle impeding device, so that the beam is not occluded by said device.

The beam may be arranged to pass through the charged particle impeding device, the analyser further comprising a guard electrode located between the charged particle impeding device and the charged particle detector, and overlying at least the area of the charged particle impeding device through which the beam passes.

The detector may comprise at least one pair of electrodes, the electrodes of the pair being spaced apart by a distance that is substantially less than the spacing between the source and the detector, the electrodes of the pair being maintained at different potentials, and the source being maintained at a potential different from the potential of the electrodes, the potentials being selected such that charged particles emitted by the source are attracted from the source towards each of the pair of electrodes, such that secondary charged particles adjacent the detector are accelerated to energies sufficient to ionise the gas.

According to a second aspect, the present invention provides a method for analysing ionising primary particles emitted by a source, wherein an ionisable gas is located between the source and a charged particle detector, and a charged particle impeding device is located between the source and the detector; the method comprising maintaining the charged particle impeding device at a potential to impede the passage of secondary electrons generated by primary charged particles ionising the gas and pass uncharged primary particles and detecting, at the charged particle detector, charged particles formed by at least the ionisation of the gas by the uncharged primary particles.

The step of detecting charged particles may be repeated whilst the charged particle impeding device is maintained at a range of different potentials.

The method may further comprise the step of maintaining the charged particle impeding device at a potential to allow the substantially unimpeded passage of both charged particles and uncharged particles and detecting, at the charged particle detector, charged particles formed by the ionisation of the gas by both the charged ionising particles and the uncharged ionising particles.

Embodiments of the present invention will now be described by way of example only with reference to the accompanying drawings, wherein.

The present inventors have realised that ionising particle analysers can be improved by adding a device arranged to impede the path of charged particles from the ionising source, whilst allowing the relatively unimpeded passage of uncharged ionising particles. For instance, in emission EXAFS, the implementation of such a device allows the separation of the fluorescent yield (FY) component and the total electron yield (TEY) component of the signal, allowing the FY component to be measured independently. The FY signal is that signal originating due to the source emitting an X-ray instead of an Auger electron. The FY signal is particularly small for low Z (atomic number) samples for low energy X-rays, with the FY signal being normally swamped by the TEY signal.

The FY component provides information about the structure of the sample material at depths of up to a few microns. In contrast, the TEY component only provides information about the structure of the material close to the surface (i.e. of the order of tens of nanometres). Consequently, the provision of a technique that allows quasi-independent FY and TEY measurements leads to improved information about the structure of the sample at various depths below the surface.

A preferred embodiment of the invention will now be described with reference to the accompanying drawings.

Figure 1:
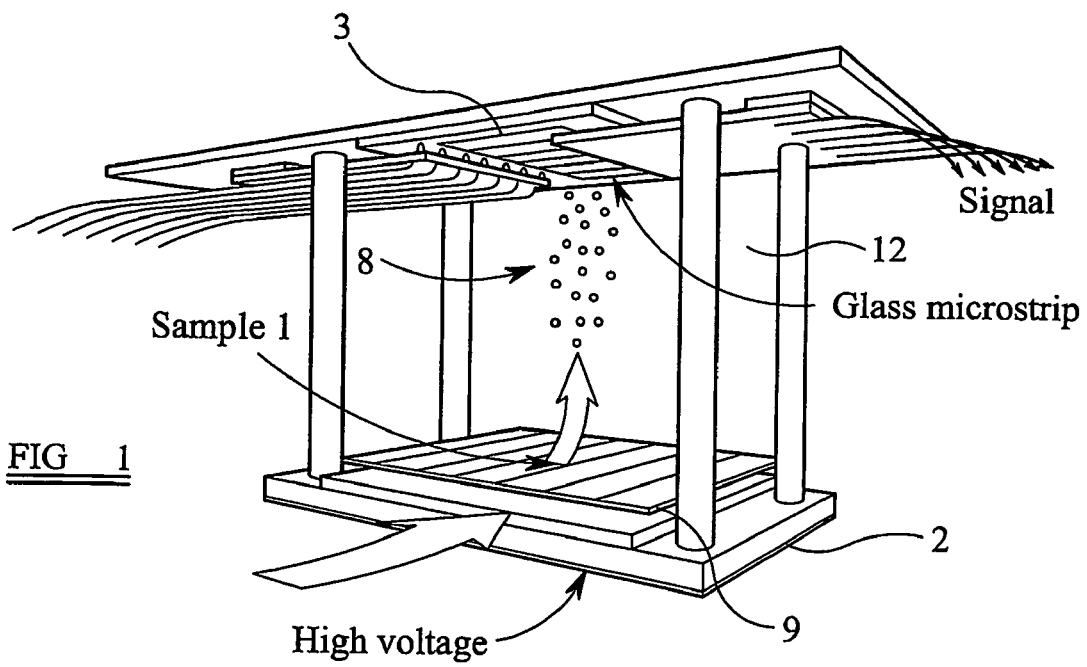
FIG. 1 is a schematic perspective view of an ionising particle analyser according to a first embodiment of the present invention.

Referring to FIG. 1, a sample 1 is positioned on a planar base 2. A detector 3 is provided directly above the sample 1 and the base 2. The detector 3 is planar, and lies in a plane which is parallel to the plane of the sample 1 and the base 2.

Figure 2:
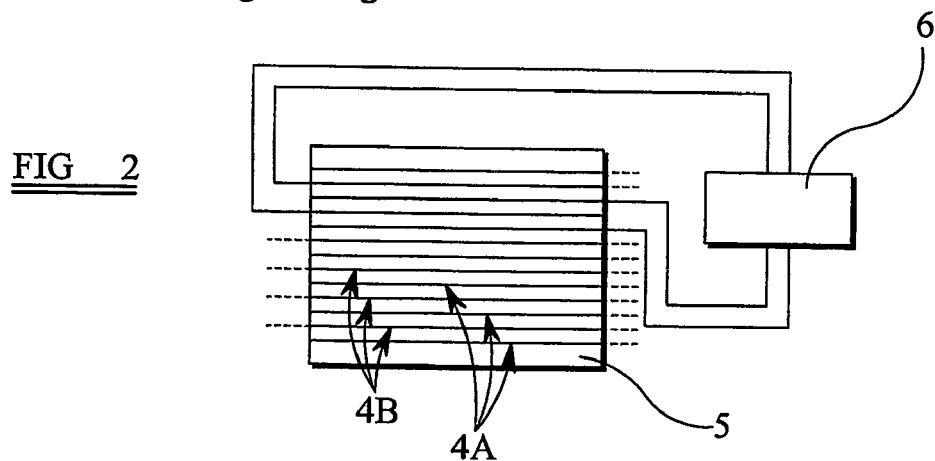
FIG. 2 is a schematic view of a charged particle detector incorporated in the analyser of FIG. 1.

The detector 3, shown in more detail in FIG. 2, comprises a series of parallel electrodes 4 deposited onto a semi-conducting glass plate 5. Alternate electrodes 4A and 4B on the microstrip are held at positive and negative relative voltages, to provide a pattern of anodes and cathodes. The positive electrodes 4A are each of equal width, and lithographic techniques may be used to produce electrodes 4 as little as 5 microns wide. Each electrode is connected to a detection circuit 6 which monitors the electrical signal from that electrode 4A.

The base 2 and sample 1, shown in FIG. 1, are held at a constant potential which is more negative than the potential of the negative electrodes 4 of the detector 3, so that all of the electrodes 4 of the detector 3 are at a positive potential relative to the base 1 and sample 2.

In this embodiment, the charged particle impeding device takes the form of a grid 9. The grid 9 is planar, and located in a plane substantially parallel to the plane of the sample 1 and base 2. Typically, the grid 9 will be spaced about 0.5 mm to 1 mm from the sample 1. The grid 9 takes the form of a series of parallel, longitudinally extending bars or wires. Typically, the separation between the bars or wires is greater than the width of each bar or wire. For instance, the wires may be 100 microns in diameter, with a 1 mm separation or pitch between each wire, thus giving the wire grid a 10:1 mark-space ratio. The grid is Typically formed of a conductive material, such as copper, allowing the grid 9 to be maintained at a predetermined potential relative to the base 1 and sample 2, and relative to the electrodes 4 of the detector 3.

The sample 1, detector 3 and grid 9 are held in a sealed chamber (not shown) which is filled with gas 12, which is predominantly a noble gas chosen to suit the sample under study. The gas 12 may also contain a quenching gas such as Isobutane, Typically at a level of around 10 percent, which acts to stop continuous electrical breakdown in the atmosphere.

In use, X-rays are generated using a synchrotron or other means (not shown), and X-rays with a desired energy are selected from the synchrotron and directed as a beam 7 onto the surface of the sample 1. The X-rays approach the sample 1 from a direction which is perpendicular to the orientation of the electrodes 4 on the detector 3. The angle formed between the beam of X-rays 7 and the surface of the sample 1 is small, so that the X-rays impinge on the surface of the sample 1 at a glancing angle. The area on the surface of the sample 1 onto which the X-rays impinge is varied by changing the angle between the X-rays and the sample 1.

Preferably, the grid 9 is placed at sufficient distance from the sample and/or the glancing angle of the beam of X-rays 7 is shallow enough, such that the beam 7 is not incident upon the grid 9, but passes between the parallel surfaces of the grid 9 and the base 2 to impinge on the surface of the sample 1.

Figure 5:
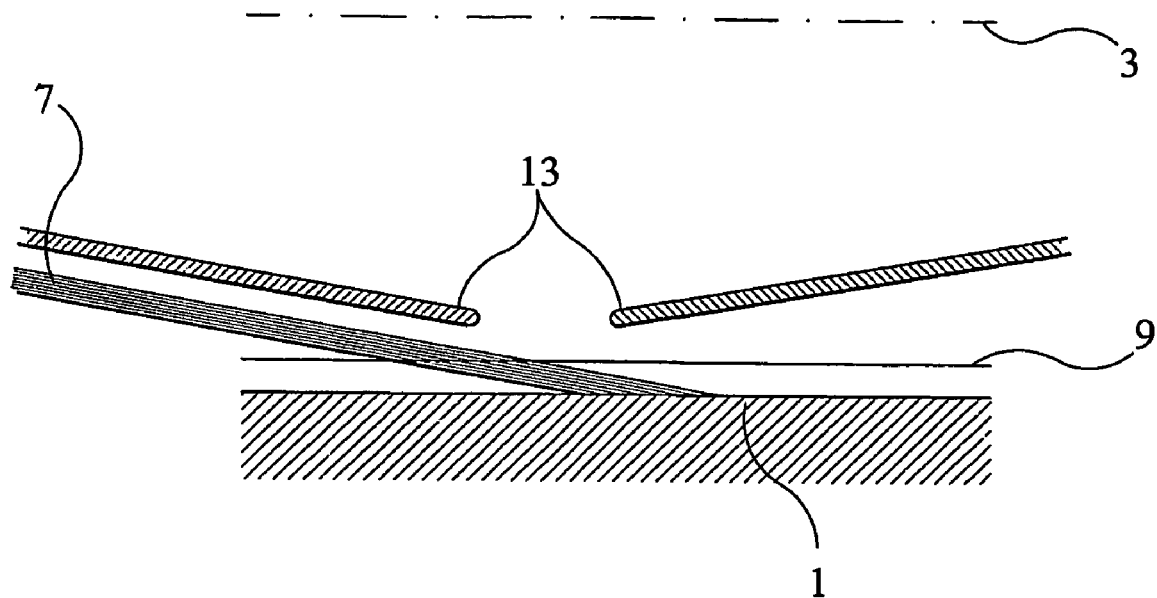
FIG. 5 is a schematic cross sectional view of an ionising particle analyser according to a second embodiment of the present invention.

If the beam 7 is arranged to impinge upon the grid 9 (such that the beam 7 is partially occluded by the grid 9), then it is preferable that the longitudinally extending bars or wires of the grid extend substantially parallel to the direction of the beam 7, so as to minimise the surface area of the grid seen by the beam 7. Preferably, as indicated in FIG. 5, if the beam 7 is arranged to impinge upon the grid 9, then at least one guard electrode 13 is placed between the grid 9 and the detector 3 for screening of the detector from detecting unwanted particles. The guard electrode 13 may take the form of a rigid sheet of an electrically conductive material. The guard electrode 13 will typically be held at the same potential as the grid 9. The guard electrode 13 is arranged to overlie at least the portion of the grid 9 through which the beam passes. Preferably, the electrode 13 is arranged to be substantially parallel to the path of the beam. The electrode 13 can be arranged to overlie all portions of the beam that are between the grid 9 and the detector 3. The beam may ionise the gas or cause the release of particles when it hits the grid 9. The guard electrode 13 can act in general to prevent such particles being detected at the detector 3, by either blocking the particles or secondary electrons generated by such particles. If desired, as illustrated in FIG. 5, the guard electrode 13 may be placed so as to only allow the particles emitted from the beam footprint on the sample 1 to reach the detector 3 e.g. the electrode 13 may also be placed so as to prevent spurious signals from any reflected beam passing through the grid/gas reaching the detector.

Electrons 11 at the surface of the sample 1 acquire energy from the X-ray beam 7, and are emitted from the sample 1. Equally, photons 10 will be emitted from the surface of the sample 1 with energy acquired from the X-ray beam 7.

In a first configuration, the grid 9 is maintained at a negative potential with respect to the sample 1.

Figure 3A:
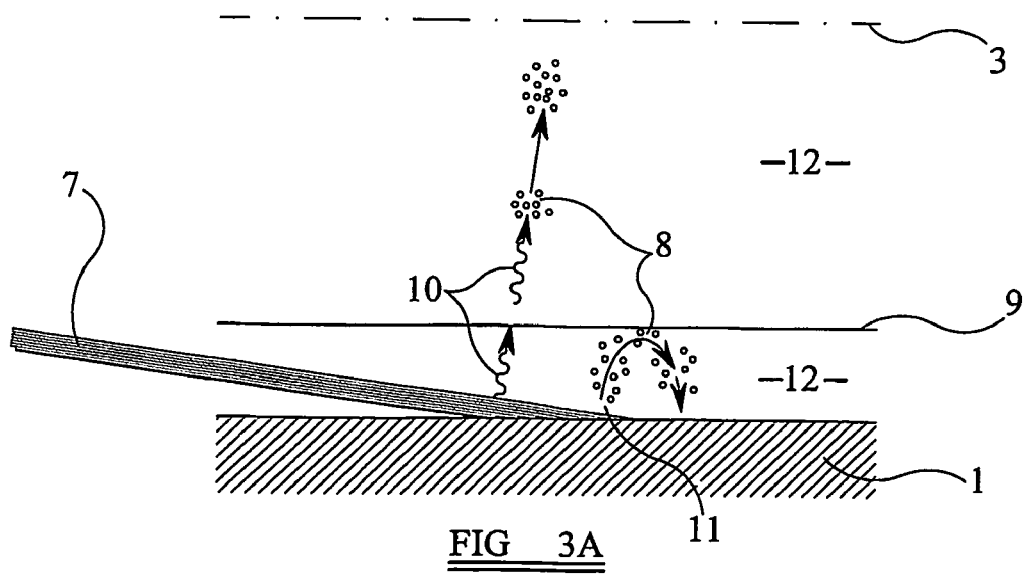
FIGS. 3A and 3B are schematic cross sectional views illustrating different operational modes of the embodiment shown in FIG. 1.

The effective cross-sectional area of the gas (and hence the likelihood of a particle colliding with and ionising the gas particles) depends upon the pressure of the gas, and the material forming the gas. If the cross-sectional area of the gas is large enough, all of the electrons 11 emitted from the surface will ionise the gas adjacent the surface of the sample 1, forming a cloud of electrons 8. In such an instance, as shown in FIG. 3A, the grid 9 is maintained at a potential sufficient to repel the secondary electrons ionised by the TEY electrons back towards the sample 1.

In each case, the surface of the sample is normally conducting, to prevent the build-up of charge from the repelled electrons. Further, in each case, the photons 10 emitted from the sample 1 pass relatively unimpeded through the grid 9. The photons 10 subsequently ionise the gas, to form a cloud of electrons 8. This cloud of electrons is subsequently detected by the charged particle detector, providing a measurement of the fluorescent yield component, without the TEY component.

Preferably, the gas pressure and mixture is carefully chosen to ensure that the uncharged particles emitted from the sample (e.g. the photons 10) will ionise the gas between the grid 9 and the detector 3 whilst the other sources of ionisation (from charged particles emitted from the sample 1) are suppressed by the grid 9. The X-ray-induced secondary electrons 8 from the ionised gas will then be detected by the charged particle detector, providing a signal indicative only of the FY component.

Figure 3B:
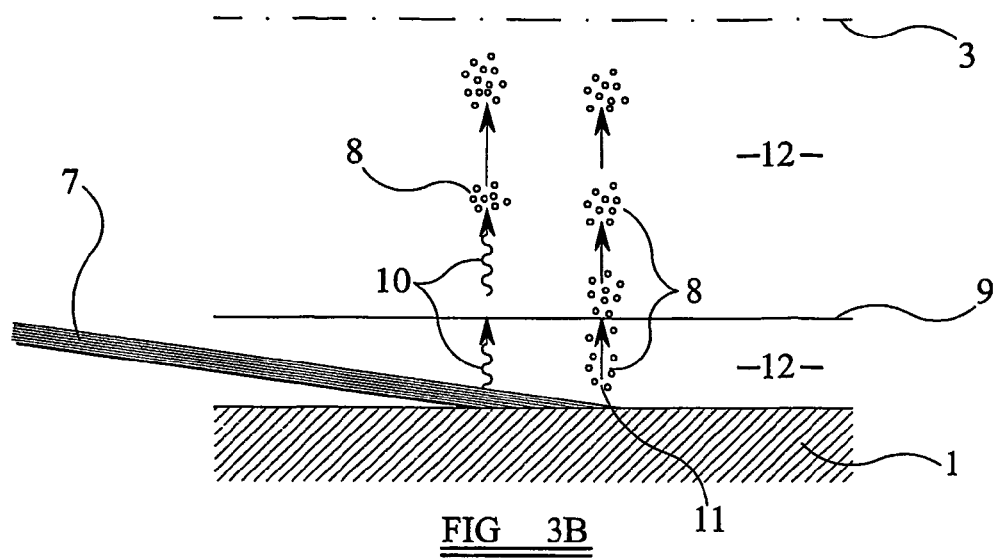

In a second, alternative configuration shown in FIG. 3B, the grid 9 is maintained at a potential that does not impede the path of the charged particles e.g. the grid 9 is held at a slightly positive potential compared to the sample 1 (but at a lower positive potential than the detector 3). The result is that both the photons 10 and the electrons 11 emitted from the surface will ionise the gas, to form clouds of electrons 8. The clouds of electrons are in turn detected by the charged particle detector 3. Thus, the signal from the charged particle detector is indicative of both the FY and the TEY components.

Figure 4:
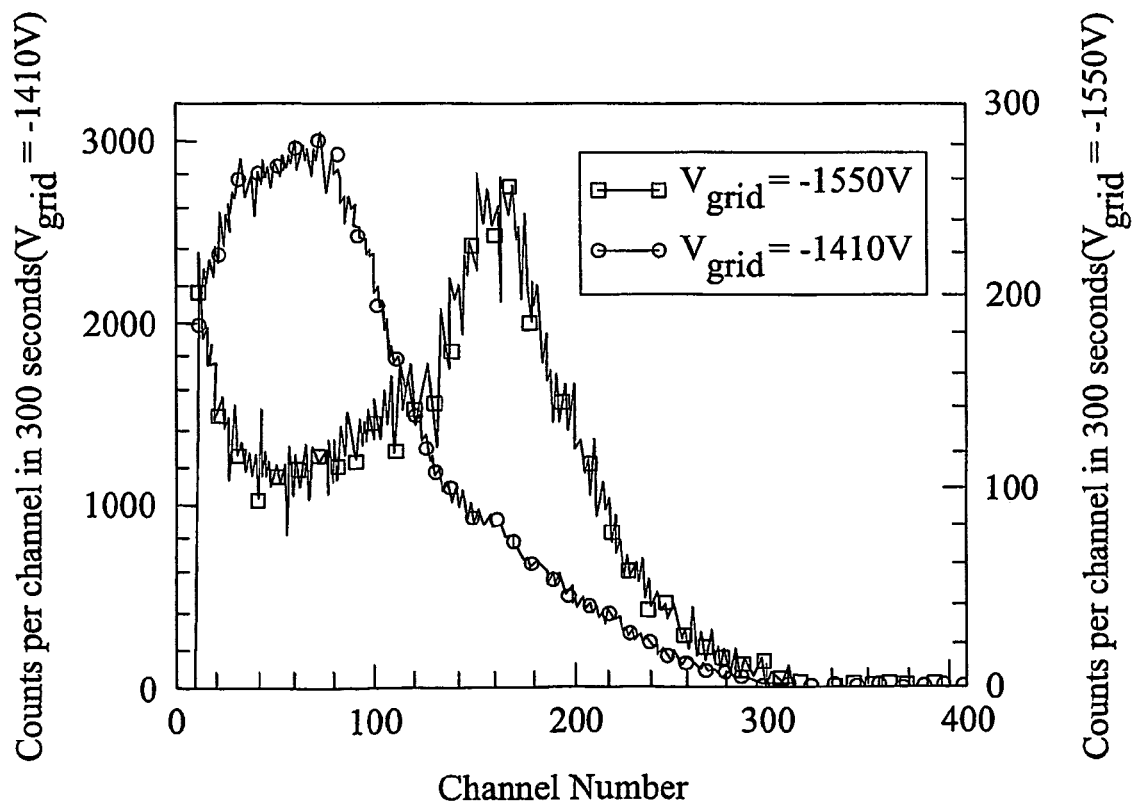
FIG. 4 is a chart indicating the output spectrum from the charged particles detector for different voltages applied to the charged particle impeding device.

By way of example, FIG. 4 shows a chart indicating the data from the detector 3 for different voltages of the grid 9. The data is derived from an experiment using a beam of 8 keV X-rays incident on a Titanium sample. The gas used was a mixture of 75% helium (He) and 25% of Isobutane (IB). The sample 1 was held at a potential of −1500V (all voltages are relative to the potential at electrodes 4A), while the detector potential on electrodes 4B was held at −719V, giving a gas avalanche gain of 2000, so allowing each event to be detected. FIG. 4 shows the pulse height spectra observed from the electrodes 4A in two cases: (i) when the grid 9 was set at −1410V, so permitting the detection of both the TEY and the FY (circles and left hand ordinate), and (ii) when the grid 9 was set to −1550V, such that the TEY is almost totally suppressed and the previously invisible Titanium FY peak is clearly observed (squares and right-hand ordinate). The spectra illustrate the counts per channel in each 300 second interval. The channel number of FIG. 4 is proportional to the energy of each of the primary particles histogrammed in the figure. The difference in the ordinate scales should be noted.

In general, the density of the gas, the voltage gradient through which the electrons pass, and the initial kinetic energy of the electrons determine whether the initial interactions of the particles with the gas are close to the surface of the sample 1 or spread throughout the gas as the electrons travel towards the detector 3. The density of the gas and the voltage maintained at the detector 3 may be optimised to measure position or energy resolution of both the charged and uncharged ionising particles emitted from the sample 1.

The negative potential of the sample 1 and base 2, relative to the detector 3, causes each electron cloud 8 to drift towards the detector 3 (the drifting electrons are shown as 8 in the Figures). Information relating to the position at which the electrons were emitted from the sample 1 is retained during drift of the electron cloud 8 since the direction of drift is perpendicular to the surface of the sample 1, and the electrons do not have sufficient kinetic energy to deviate significantly from a position directly above the point from which they were emitted.

The pattern of parallel anodes and cathodes 4 provided on the detector 3 does not affect the drift of the electron cloud until it is immediately adjacent the detector 3. This is because the electric field produced as a consequence of the close proximity of the anodes and cathodes 4 on the detector 3 is very localised. As the electrons approach the detector 3, they are accelerated towards the anodes by the localised electric field, whose intensity increases rapidly adjacent the detector 3. The acceleration of the electrons provides them with sufficient energy to ionise the gas in the chamber, producing more electrons which themselves cause further ionisation. In this way, the electrons emitted from the sample 1 produce an avalanche of electrons from the gas adjacent the detector 3. The generation of an avalanche of electrons is useful because it increases the electrical signal produced at the detector 3 to a level which may be accurately measured. The gain in signal produced by the avalanche is controlled to ensure that the final number of electrons detected is proportional to the initial number of electrons emitted from the sample 1.

Localising the avalanche of electrons in a region immediately adjacent the detector 3 is advantageous because the electrons produced by ionisation of the gas remain localised, and spatial information relating to the electrons emitted from the sample 1 is retained. The spatial information referred to is simply the position at which electrons were emitted from the sample relative to a front and a back end of the sample 1.

The front and back ends of the sample 1 are defined as being the ends of the sample 1 which are nearest and furthest respectively from the origin of the X-ray beam 7. The relative strength of the signals received from each of the electrodes 4A on the detector 3 is used to identify the point at which the X-ray beam 7 interacted with the surface of the sample 1.

The strength of the electric field adjacent the detector 3 is determined by the potentials applied to the anodes and cathodes 4A and 4B of the detector 3, and also by the distance between them. Reducing the spacing between the anodes and cathodes will increase the gradient of the electric field adjacent the detector 3, and the applied potential needed to produce a desired acceleration of electrons will be correspondingly reduced. Increasing the density of electrodes 4 on the detector 3 will also increase the spatial resolution of the detector 3.

Although the above embodiments refer solely to the detection of electrons, it should be understood that the invention may be used for the detection of other positively or negatively charged particles.

Equally, it will be appreciated that whilst the above apparatus has been described in conjunction with an emission EXAFS experiment, such an ionising particle analyser may be used in conjunction with any source of ionising particles, in which both charged particles and uncharged particles are emitted that can ionise a gas. For instance, embodiments of the present invention could be used in X-ray fluorescence analysis, particularly with low energy X-rays.

Further, embodiments could be used in configuration with any gas ionisation detector e.g. a wire converter.

The invention claimed is:

1. Ionising particle analyser comprising:
a source of ionising primary particles;
a charged particle detector;
an ionisable gas located between the source and the detector; and
wherein the analyser further comprises a charged particle impeding device located between the source and the detector, and arranged to be maintained in a first configuration at a potential to impede the passage of secondary electrons generated by charged primary particles ionising the gas and pass uncharged particles.

2. An analyser according to claim 1, wherein the charged particles comprise electrons and the uncharged particles comprise photons.

3. An analyser according to claim 1, wherein the charged particle impeding device is held at a potential to repel the charged secondary electrons generated in the gas by the primary particles.

4. An analyser according to claim 1, wherein the charged particle impeding device comprises at least one bar lying in a plane substantially parallel to a surface of the sample.

5. An analyser according to claim 1, wherein the charged particle impeding device comprises a grid comprising a plurality of substantially parallel bars.

6. An analyser according to claim 1, wherein the charged particle impeding device is further arranged to be maintained in a second configuration that allows the substantially unimpeded passage of both charged particles and uncharged particles.

7. An analyser according to claim 1, wherein the charged particle impeding device is located within the ionisable gas, and spaced from the source such that charged particles emitted from the source will have been substantially completely converted to ionised gas electrons prior to being incident upon the charged particle impeding device.

8. An analyser according to claim 1, wherein the detector comprises at least one pair of electrodes, the electrodes of the pair being spaced apart by a distance that is substantially less than the spacing between the source and the detector, the electrodes of the pair being maintained at different potentials, and the source being maintained at a potential different from the potential of the electrodes, the potentials being selected such that charged particles emitted by the source are attracted from the source towards each of the pair of electrodes, such that secondary charged particles adjacent the detector are accelerated to energies sufficient to ionise the gas.

9. An analyser according to claim 1, wherein the source is a sample and means are provided for exposing the sample to a beam of radiation, the energy of which is sufficient to cause ionising particles to be emitted from the sample.

10. An analyser according to claim 9, wherein the exposing means comprises an X-ray source.

11. An analyser according to claim 9, wherein the beam is arranged to pass between the source and the charged particle impeding device, so that the beam is not occluded by said device.

12. An analyser according to claim 9, wherein the beam is arranged to pass through the charged particle impeding device, the analyser further comprising a guard electrode located between the charged particle impeding device and the charged particle detector, and overlying at least the area of the charged particle impeding device through which the beam passes.

13. An analyser according to claim 9, wherein the sample defines a surface which is substantially planar and the beam is directed towards the sample in a direction inclined to a normal to the sample surface.

14. An analyser according to claim 13, wherein the beam is directed at a glancing angle relative to the sample surface.

15. A method for analysing ionising primary particles emitted by a source, wherein an ionisable gas is located between the source and a charged particle detector, and a charged particle impeding device is located between the source and the detector;

the method comprising:
maintaining the charged particle impeding device at a potential to impede the passage of secondary electrons generated by charged primary particles ionising the gas and pass uncharged primary particles; and
detecting, at the charged particle detector, charged particles formed by at least the ionisation of the gas by the uncharged primary particles.

16. A method as claimed in claim 15, wherein the step of detecting charged particles is repeated whilst the charged particle impeding device is maintained at a range of different potentials.

17. A method as claimed in claim 15, further comprising the step of:
maintaining the charged particle impeding device at a potential to allow the substantially unimpeded passage of both charged particles and uncharged particles; and
detecting, at the charged particle detector, charged particles formed by the ionisation of the gas by both the charged ionising particles and the uncharged ionising particles.

* * * * *

UNITED STATES PATENT AND TRADEMARK OFFICE
CERTIFICATE OF CORRECTION

PATENT NO.        : 7,432,501 B2
APPLICATION NO. : 10/571183
DATED             : October 7, 2008
INVENTOR(S)       : James Edmond Bateman and Gareth Derbyshire It is certified that error appears in the above-identified patent and that said Letters Patent is hereby corrected as shown below:

On the Title Page, Item (73) should read correction of Assignee to: The Science and Technology Facilities Council, Warrington (GB)

Signed and Sealed this

Seventh Day of April, 2009

JOHN DOLL
*Acting Director of the United States Patent and Trademark Office*